(12) United States Patent
Xu et al.

(10) Patent No.: US 9,850,291 B2
(45) Date of Patent: Dec. 26, 2017

(54) GENES ENCODING NOVEL LIPID TRANSPORTERS AND THEIR USE TO INCREASE OIL PRODUCTION IN VEGETATIVE TISSUES OF PLANTS

(71) Applicant: Brookhaven Science Associates, LLC, Upton, NY (US)

(72) Inventors: Changcheng Xu, Calverton, NY (US); Jilian Fan, Calverton, NY (US); Chengshi Yan, Coppell, TX (US); John Shanklin, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 233 days.

(21) Appl. No.: 14/719,486

(22) Filed: May 22, 2015

(65) Prior Publication Data

US 2015/0337017 A1    Nov. 26, 2015

Related U.S. Application Data

(60) Provisional application No. 62/002,520, filed on May 23, 2014.

(51) Int. Cl.
 *C12N 15/82* (2006.01)
 *C07K 14/415* (2006.01)

(52) U.S. Cl.
 CPC ........ *C07K 14/415* (2013.01); *C12N 15/8247* (2013.01)

(58) Field of Classification Search
 None
 See application file for complete search history.

(56) References Cited

PUBLICATIONS

Fan et al 2015 (The Plant Cell 27: p. 2941-2955).*
Sessions 2002 (The Plant Cell 14: p. 2985-2994).*
Awai, K., et al., "A phosphatidic acid-binding protein of the chloroplast inner envelope membrane involved in lipid trafficking," PNAS, vol. 103, No. 28, pp. 10817-10822 (2006).
Lu, B., et al., "A Small ATPase Protein of Arabidopsis, TGD3, Involved in Chloroplast Lipid Import," J. Biol. Chem. (2007) 282, pp. 35945-35953.
Durrett, T. P., et al., "Harnessing Plant Biomass for Biofuels and Biomaterials: Plant triacylglycerols as feedstocks for the production of biofuels," The Plant Journal (2008) 54, pp. 593-607.
Kelly, A. A., "The Sugar-Dependent1 lipase limits triacylglycerol accumulation in vegetative tissues of Arabidopsis," Plant Physiology Preview, (2013) and Plant Physiology (2013) vol. 162, pp. 1282-1289.
Ohlrogge, J., "Expanding the contribution of plant oils as biofuels: The seeds of green energy," The Biochemical Society, Bioenergy Features (2011) pp. 34-38.
Troncoso-Ponce, M. A., "Lipid turnover during senescence," J. Plant Science, 205-206 (2013) pp. 13-19.
Xu, C., et al., "Mutation of the TGD1 Chloroplast Envelope Protein Affects Phosphatidate Metabolism in Arabidopsis," The Plant Cell, vol. 17, pp. 3094-3110, (2005).
Xu, C., et al., "Lipid Trafficking between the Endoplasmic Reticulum and the Plastid in Arabidopsis Requires the Extraplastidic TGD4 Protein," The Plant Cell, vol. 20, pp. 2190-2204 (2008).

* cited by examiner

*Primary Examiner* — Matthew Keogh
(74) *Attorney, Agent, or Firm* — Dorene M. Price

(57) ABSTRACT

The present invention discloses a novel gene encoding a transporter protein trigalactosyldiacylglycerol-5 (TGD5), mutations thereof and their use to enhance TAG production and retention in plant vegetative tissue.

12 Claims, 5 Drawing Sheets

TGD5 (At1g27695) genomic sequence (SEQ ID NO: 1)

```
   1 TCTTCACCTT TCTTCTCTTG CTTTCAGGGC TTGCGATTTT AAGTGGGGGA GGTAGAGAGA
  61 GCAATCTACC AGATTCACCG ATTACCAACA ACAAACAAGG TATCATCGGG TAATTCAGAT
 121 TCGCAATTTC TGCTCATTTG AATTTATAGA TTCCTAAATT GGTTTCTTTT TTTTTCTTGT
 181 GAAGATCACT ATGGTGCTCT CTGACTTCAC TGGAGTCGGT GTTGGATTTG GTAATGCCCC
 241 CATTCGCAAT TGTTTTCTCC TTTTAATTTT GATTGGAATC GTAATTTAGT TATTGGAATT
 301 CATAGGGTTC GGTGTTGGTT GTGGATTGG CGTTGGATGG GGTTTTTGGAG GTTCGTTCTC
 361 AACTTCTCTC TTTTTCTGCT TTTACTTGAA CAAAATCTGG ACTGAATTAC AAGATAATTC
 421 TATTGGAACA ATTCTCCTTGC TAGTTGCTAT GGGATGTGCA ATGCACTCTG CTGTGCTTGT
 481 TTAGTTTTGT GATCATATTG CTTAATGTCT CTTATAGAGA TTATCAACTC CTACATATCA
 541 TCTTTACTCA AATGCTTCTT CTTTCCTAGC TAATGGTTGC TTAAACGCAT AGCTAGTATC
 601 AGTTGCGCTT ACATTTTGAT GGATTCATAC TATTTTGCAA ACCTACTGAA TTGGAGATTT
 661 CCGTTGCTTT CATGCAGGAA TGCCTATGAA CATCTTAGGT GTTGGTGCTG GTAAGCATTT
 721 CAAACTTCTA CTTCAAATAT CCCACACTCG CATAGATACA CACCGAGCAG GTTTTTCCTA
 781 AATTCTAATT ACGTAACTTA TGCGTCTGGT ATTTGACAAA GGTGGCGGTT GCGGGTGGG
 841 TTTGGGCCTC GGGTGGGGTT TCGGGACTGC GTTTGGGAGT CACTATCGTT CATCTAGACT
 901 TACATTTCAA GGCATCGAGT TAGAGACTGC CGATAAACGG GAGGAGGTGG TGGCTAACAT
 961 GTCCAAAAAC TCCACTTAAG CAGTCGTGTG CTTCAATACT CTGCTCGGAT TGATTGTAAA
1021 AGAATTCTGA CACCTTTTCT TATTTCTCAA TGAAACGGTT ACTTCAAATA ATCCAATACG
1081 AAATGCATTT CGTATTCTG AATTGTCATT TTTAGAAGGT TCCACTTC
```

TGD5 (At1g27695) protein sequence (SEQ ID NO: 2)

```
  1 MVLSDFTGVG VGFGFGVGCG FGVGWGFGGM PMNILGVGAG GGCGVGLGLG
 51 WGFGTAFGSH YRSSRLTFQG IELETADKRE EVVANMSKNS T
```

Fig. 1 tgd5-1 mutant sequence (SEQ ID NO: 3)

```
   1  TCTTCACCTT TCTTCTCTTG CTTTCAGGGC TTGCGATTTT AAGTGGGGGA GGTAGAGAGA
  61  GCAATCTACC AGATTCACCG ATTACCAACA ACAAACAAGG TATCATCGGG TAATTCAGAT
 121  TCGCAATTTC TGCTCATTTG AATTTATAGA TTCCTAAATT GGTTTCTTTT TTTTTCTTGT
 181  GAAGATCACT ATGGTGCTCT CTGACTTCAC TGGAGTCGGT GTTGGATTTG GTAATGCCCC
 241  CATTCGCAAT TGTTTTCTCC TTTTAATTTT GATTGGAATC GTAATTTAGT TATTGGAATT
 301  CATAGGGTTC GGTGTTGGTT GTGGATTTGG CGTTGGATGG GGTTTTGGAG GTTCGTTCTC
 361  AACTTCTCTC TTTTTCTGCT TTTACTTGAA CAAAATCTGG ACTGAATTAC AAGATAATTC
 421  TATTGGAACA ATTCTCTTGC TAGTTGCTAT GGGATGTGCA ATGCACTCTG CTGTGCTTGT
 481  TTAGTTTTGT GATCATATTG CTTAAATGTCT CTTATAGAGA TTATCAACTC CTACATATCA
 541  TCTTTACTCA AATGCTTCTT CTTTCCTAGC TATTGGTTGC TTAAACGCAT AGCTAGTATC
 601  AGTTGCGCTT ACATTTTGAT GGATTCATAC TATTTTGCAA ACCTACTGAA TTGGAGATTT
 661  CCGTTGCTTT CATGCAGGAA TGCCTATGGA CATCTTAGGT GTTGGTGCTG GTAAGCATTT
 721  CAAACTTCTA CTTCAAATAT CCCACACTCG CATAGATACA CACCGAGCAG GTTTTTCCTA
 781  AATTCTAATT ACGTAACTTA TGCGTCTGGT ATTTGACAAA GGTGACGGTT GCGGGTGGG
 841  TTTGGCCCTC GGGTGGGGTT TCGGGACTGC GTTTGGGAGT CACTATCGTT CATCTAGACT
 901  TACATTTCAA GGCATCGAGT TAGAGACTGC CGATAAACGG GAGGAGGTGG TGGCTAACAT
 961  GTCCAAAAAC TCCACTTAAG CAGTCGTGTG CTTCAATACT CTGCTCGGAT TGATTGTAAA
1021  AGAATTCTGA CACCTTTTCT TATTCTCAA TGAAACGGTT ACTTCAAATA ATCCAATACG
1081  AAATGCATTT CTGTATTCTG AATTGTCATT TTTAGAAGGT TCCACTTC
``` tgd5-1 mutant protein sequence (SEQ ID NO: 4)

```
  1  MVLSDFTGVG VGFGFGVGCG FGVGWGFGGM PMNILGVGAG DGCGVGLGLG
                                                   ‾
 51  WGFGTAFGSH YRSSRLTFQG IELETADKRE EVVANMSKNS T
```

Fig. 2

SEQUENCE LISTING

<160> NUMBER OF SEQ ID NOS: 9

<210> SEQ ID NO 1
<211> LENGTH: 1128
<212> TYPE: DNA
<213> ORGANISM: Arabidopsis thaliana

<400> SEQUENCE: 1

```
tcttcacctt tcttctcttg ctttcagggc ttgcgatttt aagtggggga ggtagagaga      60
gcaatctacc agattcaccg attaccaaca acaaacaagg tatcatcggg taattcagat     120
tcgcaatttc tgctcatttg aatttataga ttcctaaatt ggtttctttt tttttcttgt     180
gaagatcact atggtgctct ctgacttcac tggagtcggt gttggatttg gtaatgcccc     240
cattcgcaat tgttttctcc ttttaatttt gattggaatc gtaatttagt tattggaatt     300
catagggttc ggtgttggtt gtggatttgg cgttggatgg ggttttggag gttcgttctc     360
```

```
aacttctctc tttttctgct tttacttgaa caaaatctgg actgaattac aagataattc      420
tattggaaca attctcttgc tagttgctat gggatgtgca atgcactctg ctgtgcttgt      480
ttagttttgt gatcatattg cttaatgtct cttatagaga ttatcaactc ctacatatca      540
tctttactca aatgcttctt ctttcctagc taatggttgc ttaaacgcat agctagtatc      600
agttgcgctt acattttgat ggattcatac tattttgcaa acctactgaa ttggagattt      660
ccgttgcttt catgcaggaa tgcctatgaa catcttaggt gttggtgctg gtaagcattt      720
caaacttcta cttcaaatat cccacactcg catagataca caccgagcag ttttttccta      780
aattctaatt acgtaactta tgcgtctggt atttgacaaa ggtggcggtt gcggggtggg      840
tttgggcctc gggtggggtt tcgggactgc gtttgggagt cactatcgtt catctagact      900
tacatttcaa ggcatcgagt tagagactgc cgataaacgg gaggaggtgg tggctaacat      960
gtccaaaaac tccacttaag cagtcgtgtg cttcaatact ctgctcggat tgattgtaaa     1020
agaattctga cacctttttct tatttctcaa tgaaacggtt acttcaaata atccaatacg     1080
aaatgcattt ctgtattctg aattgtcatt tttagaaggt tccacttc                   1128
```

<210> SEQ ID NO 2
<211> LENGTH: 91
<212> TYPE: PRT
<213> ORGANISM: Arabidopsis thaliana

<400> SEQUENCE: 2

```
Met Val Leu Ser Asp Phe Thr Gly Val Gly Val Gly Phe Gly Phe Gly
1               5                   10                  15

Val Gly Cys Gly Phe Gly Val Gly Trp Gly Phe Gly Gly Met Pro Met
            20                  25                  30

Asn Ile Leu Gly Val Gly Ala Gly Gly Gly Cys Gly Val Gly Leu Gly
        35                  40                  45

Leu Gly Trp Gly Phe Gly Thr Ala Phe Gly Ser His Tyr Arg Ser Ser
    50                  55                  60

Arg Leu Thr Phe Gln Gly Ile Glu Leu Glu Thr Ala Asp Lys Arg Glu
65                  70                  75                  80

Glu Val Val Ala Asn Met Ser Lys Asn Ser Thr
                85                  90
```

<210> SEQ ID NO 3
<211> LENGTH: 1128
<212> TYPE: DNA
<213> ORGANISM: Arabidopsis thaliana

<400> SEQUENCE: 3

```
tcttcacctt tcttctcttg ctttcagggc ttgcgatttt aagtgggga ggtagagaga       60 gcaatctacc agattcaccg attaccaaca acaaacaagg tatcatcggg taattcagat      120
tcgcaatttc tgctcatttg aatttataga ttcctaaatt ggtttctttt ttttctttgt      180
gaagatcact atggtgctct ctgacttcac tggagtcggt gttggatttg gtaatgcccc      240
cattcgcaat tgttttctcc ttttaatttt gattggaatc gtaatttagt tattggaatt      300
catagggttc ggtgttggtt gtggatttgg cgttggatgg ggttttggag gttcgttctc      360
aacttctctc tttttctgct tttacttgaa caaaatctgg actgaattac aagataattc      420
tattggaaca attctcttgc tagttgctat gggatgtgca atgcactctg ctgtgcttgt      480
ttagttttgt gatcatattg cttaatgtct cttatagaga ttatcaactc ctacatatca      540
tctttactca aatgcttctt ctttcctagc taatggttgc ttaaacgcat agctagtatc      600
```

```
agttgcgctt acattttgat ggattcatac tattttgcaa acctactgaa ttggagattt     660
ccgttgcttt catgcaggaa tgcctatgaa catcttaggt gttggtgctg gtaagcattt     720
caaacttcta cttcaaatat cccacactcg catagataca caccgagcag gttttcccta     780
aattctaatt acgtaactta tgcgtctggt atttgacaaa ggtgacggtt gcggggtggg     840
tttgggcctc gggtggggtt tcgggactgc gtttgggagt cactatcgtt catctagact     900
tacatttcaa ggcatcgagt tagagactgc cgataaacgg gaggaggtgg tggctaacat     960
gtccaaaaac tccacttaag cagtcgtgtg cttcaatact ctgctcggat tgattgtaaa    1020
agaattctga caccttttct tatttctcaa tgaaacggtt acttcaaata atccaatacg    1080
aaatgcattt ctgtattctg aattgtcatt tttagaaggt tccacttc                 1128
```

<210> SEQ ID NO 4
<211> LENGTH: 91
<212> TYPE: PRT
<213> ORGANISM: Arabidopsis thaliana

<400> SEQUENCE: 4

```
Met Val Leu Ser Asp Phe Thr Gly Val Gly Val Gly Phe Gly Phe Gly
1               5                   10                  15

Val Gly Cys Gly Phe Gly Val Gly Trp Gly Phe Gly Gly Met Pro Met
                20                  25                  30

Asn Ile Leu Gly Val Gly Ala Gly Asp Gly Cys Gly Val Gly Leu Gly
                35                  40                  45

Leu Gly Trp Gly Phe Gly Thr Ala Phe Gly Ser His Tyr Arg Ser Ser
            50                  55                  60

Arg Leu Thr Phe Gln Gly Ile Glu Leu Glu Thr Ala Asp Lys Arg Glu
65                  70                  75                  80

Glu Val Val Ala Asn Met Ser Lys Asn Ser Thr
                85                  90
```

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5

```
gctagttgct atgggatg                                                    18
```

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6

```
cgggtttcat tgagcaatc                                                   19
```

<210> SEQ ID NO 7
<211> LENGTH: 21
<212> TYPE: DNA
<213> ORGANISM: Artificial Sequence
<220> FEATURE:
<223> OTHER INFORMATION: Left border primer

<400> SEQUENCE: 7

-continued

```
gcgtggaccg cttgctgcaa c                                    21

<210> SEQ ID NO 8
<211> LENGTH: 29
<212> TYPE: DNA
<213> ORGANISM: Artificial Sequence
<220> FEATURE:
<223> OTHER INFORMATION: PPDAT1 primer

<400> SEQUENCE: 8
gcgtggtacc atgcccctta ttcatcgga                            29

<210> SEQ ID NO 9
<211> LENGTH: 34
<212> TYPE: DNA
<213> ORGANISM: Artificial Sequence
<220> FEATURE:
<223> OTHER INFORMATION: PDAT1 primer

<400> SEQUENCE: 9
acgtctgcag tcacagcttc aggtcaatac gctc                      34
```

GENES ENCODING NOVEL LIPID TRANSPORTERS AND THEIR USE TO INCREASE OIL PRODUCTION IN VEGETATIVE TISSUES OF PLANTS This application claims the benefit of U.S. Provisional Application 62/002,520 filed on May 23, 2014, the entire contents of which are incorporated herein by reference.

GOVERNMENT SUPPORT

This invention was made with Government support under contract numbers DE-AC02-98CH10886 and DE-SC0012704, awarded by the U.S. Department of Energy. The United States Government has certain rights in the invention.

BACKGROUND

Research and development for renewable sources of biofuels has centered in large part on efficient means of converting abundant forms of biomass (cellulose, hemicellulose, and lignin of plant cell walls) into ethanol. However, because plant oils have twice the energy (caloric) content per kilogram compared with carbohydrates and proteins, increasing oil accumulation in vegetative tissues of plants could have a greater impact on the use of biomass to generate bioelectricity or to produce biodiesel fuel and nutritional feed. In addition, using the abundant vegetative biomass as the vehicle for oil accumulation would increase the oil storage capacity of plants and would have the potential to provide abundant supplies of plant oils for biodiesel production without diverting food production resources, thereby avoiding the competition between food and biofuel.

The most readily useful forms of plant oils are the diacyl- and, more particularly, triacylglycerol fatty acid compounds (DAGs and TAGs, respectively) in which two or three fatty acid chains are esterified to a glycerol backbone. Plant seeds constitute the normal repository for TAG compound accumulation. Because plant seed oils, particularly from oilseed crops, are mostly used for food or in some instances for a source of unusual, modified fatty acid compounds as chemical feedstocks, their use as biofuel is untenable.

However, as our understanding of the pathways of lipid/fatty acid synthesis, membrane formation and intracellular lipid trafficking has increased, so has the possibility of altering plants to increase the TAG content of the non-seed (vegetative) tissues. For a recent review of lipid transport (trafficking) see C. Benning (2009) Annual Review of Cell and Developmental Biology 25:71-91, the contents of which are incorporated herein by reference. If the abundant, vegetative tissues of plants were enabled to accumulate increased amounts of oils (TAG compounds) the harvestable energy, particularly from non-food crops, could be enormously increased. Ohlrogge and Chapman postulated that "Producing biomass with 10% oil on a dry weight basis could have a major positive impact on the recovery of energy from dedicated biomass crops" (the Biochemical Society, April 2011, pp 34-38). They further speculated that planting such a crop in place of the maize that is currently planted for ethanol production (~12 million hectares) could result in 24 billion liters of biodiesel.

In developing seeds there are two pathways involved in TAG biosynthesis. The acyl-CoA-dependent pathway is catalyzed by diacylglycerol:acyl-CoA acyltransferase (DGAT) and the acyl-CoA-independent pathway by phospholipid:diacylglycerol acyltransferase (PDAT), which transfers an acyl group from phospholipids such as phosphatidylcholine (PC) to diacylglycerol. In oilseeds, TAGs are packaged in lipid droplets, which consist of a central core of TAG enclosed by a monolayer of phospholipids with a subset of specific proteins embedded therein. The most abundant proteins coating seed oil droplets are oleosins. The roles of oleosins are: 1) to stabilize lipid droplets during seed maturation and, 2) to protect TAG from hydrolysis by TAG lipases. Plant vegetative tissues normally do not express significant amounts of oleosins and they accumulate very limited amounts of storage lipids such as TAGs.

Various attempts to increase oil (TAG) storage in non-seed (vegetative) plant tissue have been described. Notable results have has been described in the works of Vanhercke, et al. (Plant Biotechnology Journal (2014) 12:231-239; and US Patent Application Publications US2013/0164798A1 and US2013/0247451A1). Alternative strategies are documented in Shanklin et al., US2014/0031573A1, which includes enlisting both acyl-CoA-dependent and acyl-CoA-independent TAG biosynthetic pathways to enhance TAG accumulation in non-seed tissue.

The approaches documented to date haven't yet produced a crop plant, neither biomass crop plant nor other crop plant, having stably heritable commercially significant improvements in the TAG accumulation in vegetative tissues. The present application provides a novel approach to enhancing oil (TAG) accumulation in the non-seed, vegetative tissues of plants.

SUMMARY

In a screen for mutants deficient in endoplasmic reticulum (ER)-to-plastid lipid trafficking we have identified a novel protein, trigalactosyldiacylglycerol-5 (TGD5), and found that plants bearing man-made (non-natural) mutations that decrease TGD5 function or activity have increased TAG production and accumulation in their vegetative tissues. Novel mutant tgd5 proteins and the mutated tgd5 genes that produce defective tgd5 proteins resulting in elevated fatty acid and TAG accumulation in plant vegetative tissues are disclosed herein. Plants expressing the defective tgd5 protein accumulate vegetative tissue TAG in amounts at least three-fold higher than otherwise identical plants. Transformation of plants carrying a mutated tgd5 gene with phospholipid:diacylglycerol acyltransferase (PDAT) expression constructs, to channel fatty acids into TAG, and oleosin (OLE1) expression constructs, to build up storage compartments for TAG, further enhances production and retention (accumulation) of TAG in the vegetative tissue. The resulting plants obtain a TAG content that is 246-fold or more increased as compared to parental plants. The TAG content of the vegetative tissues is about 8.5% of dry weight. Plants carrying a defective tgd5 gene that are transformed to over-express the WRINKLED 1 (WRI1) transcription factor, which is involved in regulation of seed oil biosynthesis, produce substantially increased amounts of TAG in vegetative tissue. It is expected that plants carrying a defective tgd5 gene and which are therefore defective in TGD5 protein, transformed to overexpress the combination of PDAT, OLE1 and WRI1 will accumulate exceptional amounts of TAG in vegetative tissue.

An alternative means to enhance accumulation of TAG in vegetative tissues of TGD5-deficient plants is to prevent breakdown of TAG by diminishing or destroying the activity of proteins and enzymes that degrade TAG. Knocking out the gene encoding sugar-dependent1 TAG lipase (SDP1) in TGD5-deficient plants further enhance accumulation of TAG in vegetative tissues.

Plants comprising a non-natural (man-made) tgd5 gene mutation, disruption or suppression that results in substantially diminished trigalactosyldiacylglycerol-5 (TGD5) protein function as compared to an otherwise identical plant expressing a wild type TGD5 gene constitute one aspect of the claimed invention. Aspects further include a plant further comprising either increased expression levels of genes encoding phospholipid:diacylglycerol acyltransferase (PDAT), or increased expression levels of genes encoding oleosin (OLE), or increased expression of WRINKLED1 (WRI1). The plant of the present invention further comprises both increased expression levels of genes encoding phospholipid:diacylglycerol acyltransferase (PDAT) and increased expression levels of genes encoding oleosin (OLE). The plant may further comprise increased expression levels of PDAT, OLE and WRI1.

The plant of the present invention may express a mutant TGD5 protein having diminished protein function as compared to wild type function; or the plant of the present invention may alternatively produce diminished amounts of functional TGD5 protein (as compared to wild type amounts of functional TGD5 protein) by suppression of expression of the TGD5 gene. The present invention contemplates that in the plants, the TGD5 protein function is diminished by at least 3-fold as compared to an otherwise identical parental plant. The present invention further contemplates that the TGD5 protein function is diminished by at least 10-fold as compared to an otherwise identical parental plant. Embodiments of the present invention further contemplate that the TGD5 protein function is undetectable in the plants. These reductions of TGD5 function may be achieved either by expressing a mutated tgd5 protein having diminished activity from a mutant tgd5 gene, or by expressing a diminished amount of normal, wild type TGD5 protein.

The tgd5 gene mutations diminish TGD5 protein activity or function and thereby enhance TAG accumulation in vegetative tissue are selected from the group consisting of point mutations, deletion mutations and insertion mutations. Suppression of TGD5 gene expression represents a phenotypic mutation that may serve to boost TAG accumulation in vegetative tissue. Plants bearing such tgd5 gene mutations or phenotypic mutations are referred to herein as TGD5-deficient plants.

The present invention further contemplates that the plant of the present invention accumulates oil in one or more vegetative non-seed tissues at levels at least 5 times greater than a wild type plant. The present invention further contemplates that the plant of the present invention accumulates oil in one or more vegetative non-seed tissues at levels at least 10 times greater than a wild type plant. The present invention further contemplates that the plant of the present invention accumulates oil in one or more vegetative non-seed tissues at levels at least 25 times greater than a wild type plant. The present invention further contemplates that the oil accumulated by the plant in one or more vegetative non-seed tissues is or comprises triacylglycerol (TAG) compounds. The present invention further contemplates that the oil is accumulated in increased amounts in one or more of vegetative non-seed tissue such as the leaves, the stems and the roots of the plants.

The present invention further contemplates that the PDAT, OLE and WRI1 proteins are over expressed as the result of expressing the genes on one or more introduced expression constructs. The present invention further contemplates that suppression of expression of the TGD5 gene may be accomplished by use of antisense, RNAi or siRNA suppression of expression of the TGD5 gene. The present invention further contemplates that mutation in, disruption of or insertion into the TGD5 gene may be accomplished by any means known in the art such as through chemical or artificially generated radiation-based mutagenesis or T-DNA insertion.

The present invention further contemplates that the plant accumulating increased amounts of TAG in non-seed tissue may be any plant selected from the group consisting of plants in which the TGD5 gene or homologs of the TGD5 gene are present, including such plants in which a TGD5 gene or homolog thereof has yet to be identified. The plant having a TGD5 gene or a homolog of a TGD5 gene may be selected from the group consisting of *Arabidopsis* sp, tomato (*Solanum lycopersicum*), potato (*Solanum tuberosum*), barley (*Hordeum* sp.), poplar (*Populus* sp.), rice (*Oryza* sp.), cucumber (*Cucumis* sp.), sorghum (*Sorghum* sp.), soybean and other legumes, grasses (e.g., *Brachypodium distachyon*), grains (e.g., *Triticum urartu*), oilseed rape (*Brassica napus*) and other *Brassica* species, and maize (*Zea* sp.). The present invention further contemplates that the progeny of the plant have the same genotype with regard to TGD5 and/or PDAT and/or OLE as the parent plant. The present invention further contemplates that the seeds have the same genotype with regard to TGD5 and/or PDAT, and/or OLE and/or WRI1 as the parent plant.

The present invention contemplates a plant comprising: a) a TGD5 gene mutation, disruption or suppression that results in substantially diminished trigalactosyldiacylglycerol-5 (TGD5) protein activity and/or function as compared to an otherwise identical plant expressing a wild type or unsuppressed TGD5 gene and further comprising b) increased expression levels of a gene encoding phospholipid:diacylglycerol acyltransferase (PDAT), c) increased expression levels of a gene encoding oleosin (OLE), and d) increased expression levels of a gene encoding the transcription factor WRINKLED 1 (WRI1).

The present invention contemplates a nucleotide sequence encoding the point mutation of the TGD5 gene (SEQ ID NO: 3, (FIG. 2)) as well as TGD5 gene sequences harboring inactivating T-DNA insertions (e.g., SEQ ID NO: 1 harboring T-DNA insertions such as those described in the Exemplification section). The present invention further contemplates a composition comprising the amino acid sequence SEQ ID NO: 4 (FIG. 2, the tgd5 mutant protein sequence) as well as nucleotide sequences (e.g., cDNA) that encode SEQ ID NO: 4.

The present invention contemplates a method for increasing production of oil in vegetative, non-seed tissues of a plant, the method comprising: providing a plant comprising: 1) a TGD5 gene mutation, disruption or suppression that results in substantially diminished trigalactosyldiacylglycerol-5 (TGD5) protein function as compared to an otherwise identical plant expressing a wild type TGD5 gene and further comprising 2) increased expression levels of genes encoding phospholipid:diacylglycerol acyltransferase (PDAT), the expression of which results in an increase in PDAT protein activity as compared to wild type expression levels of PDAT in an otherwise identical plant expressing wild type copy numbers of genes encoding PDAT, 3) increased expression levels of genes encoding oleosin (OLE), the expression of which results in an increase in OLE protein activity as compared to wild type expression levels of OLE in an otherwise identical plant expressing wild type copy numbers of genes encoding OLE and 4) increased expression levels of genes encoding the WRINKLED 1 transcription factor (WRI1), to enhance control of transcription of genes involved in storage compound biosynthesis, and growing said plant until oil has accumulated in vegetative tissues of said plant. The present invention further contemplates extracting said oil from the tissues of said plant, and particularly, extracting the oil from the leaves, stems and roots of said plant.

DESCRIPTION OF THE DRAWINGS

FIG. 1 shows TGD5 (At1g27695) genomic DNA [SEQ ID NO: 1] and TGD5 protein [SEQ ID NO: 2] sequences.

FIG. 2 shows the tgd5-1 mutant nucleotide sequence [SEQ ID NO: 3] identified in the screen of plants grown from ethyl methane sulfonate (EMS) mutagenized seeds. The tgd5-1 mutant contains a point mutation from G to A in the genomic sequence of At1g27695 at nucleotide 825 (bold and underlined). This mutation changes glycine at residue 41 of TGD5 protein [SEQ ID NO: 2] to aspartic acid (bold and underlined) in the mutant protein [SEQ ID NO: 4].

DETAILED DESCRIPTION

Figure 3:
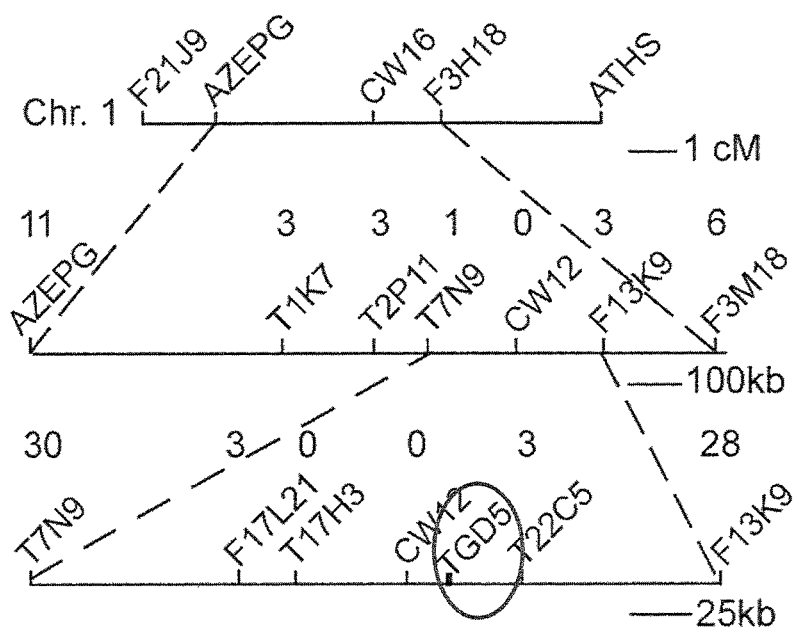
FIG. 3 shows fine mapping of TGD5 locus. The locus on chromosome 1 is shown at two different scales with increasing resolution indicated by the scale bars.

The present application is directed towards compositions and methods of increasing oil production and retention (accumulation) in plants, particularly in the non-seed, vegetative tissues of plants. The present disclosure provides that plant oil production and retention can be achieved by modification of fatty acid metabolism pathways in a subject plant. The present disclosure provides for such modification through the mutation of a gene (TGD5) encoding a trigalactosyldiacylglycerol-5 (TGD5) protein, which gene and protein had not previously been recognized as participating in lipid trafficking. Mutations of the TGD5 gene that result in lower levels of TGD5 protein function as compared to an otherwise identical plant boost accumulation of plant oils in vegetative tissues, and in particular, accumulation of oils in the form of TAGs. Diminished protein function can be obtained by reduction in function of the expressed protein or reduction in the overall levels of expression of the protein, or both. Exemplary mutations of the TGD5 gene are discussed in detail in the Exemplification section below.

The present disclosure further provides that plant oil accumulation is further enhanced by overexpression of a selection of additional genes of fatty acid metabolism pathways and genes for proteins that sequester and/or otherwise protect the oils from breakdown, degradation or usage. Oil accumulation is further enhanced by over expression of transcription factors that regulate expression of storage biosynthesis genes. Exemplary genes to further augment oil accumulation (as disclosed herein) are genes encoding phospholipid:diacylglycerol acyltransferase (PDAT), oleosin (OLE) and WRINKLED 1 (WRI1).

PDAT genes are expressed in leaves, roots, stems, developing seeds and flowers (Lu, et al., (2003) Plant Mol. Biol. 52:31-41; Stahl, et al. (2004) Plant Physiol. 135:1324-1335). Over expression of PDAT1 has been shown to enhance fatty acid (FA) and TAG synthesis in leaves (Fan, et al., (2013) The Plant Cell 25:3506-3518). PDAT participates in glycerolipid metabolism and catalyzes chemical reaction (1):

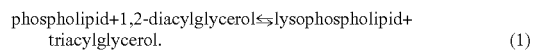

$$\text{phospholipid} + 1,2\text{-diacylglycerol} \leftrightarrows \text{lysophospholipid} + \text{triacylglycerol}. \qquad (1)$$

Oleosins are structural proteins found in vascular plant oil bodies and found in plant cells. Oleosins are proteins of 16 kDa to 24 kDa and are composed of three domains: an N-terminal hydrophilic region of variable length (from 30 to 60 residues); a central hydrophobic domain of about 70 residues and a C-terminal amphipathic region of variable length (from 60 to 100 residues).

As used therein, the term "biofuel" refers to any fuel derived from biological material(s) (e.g., from biomass). Biofuels can be substituted for petroleum based fuels. For example, biofuels may include transportation fuels (e.g., gasoline, diesel, jet fuel), heating fuels, and electricity-generating fuels. Biofuels are considered a renewable energy source.

As used herein, the term "biodiesel" means a biofuel that can substitute for diesel fuel derived from petroleum. Biodiesel can be used in internal combustion diesel engines in either a pure form, which is referred to as "neat" biodiesel, or as a mixture in any concentration with petroleum-based diesel. Biodiesel can include esters or hydrocarbons, such as alcohols, to improve combustibility, fluidity, etc.

As used herein, the term "biomass" means and includes a biological material derived from living, or recently living organisms. It most often refers to plants or plant-based materials which are specifically called lignocellulosic biomass. As an energy source, biomass can either be used directly via combustion to produce heat, or indirectly after converting it to various forms of biofuel.

Unless otherwise indicated, the accession numbers referenced herein are derived from the NCBI database (National Center for Biotechnology Information) maintained by the National Institute of Health, U.S.A. Unless otherwise indicated, the accession numbers are as provided in the database as of September 2013.

All citations (patents, patent application publications, journal articles, textbooks, and other publications) mentioned in the specification are indicative of the level of skill of those in the art to which the disclosure pertains.

It is understood that the nucleotide sequences described herein may include sequences having nucleotide substitutions in the 'wobble' coding position such that translation of the transcribed sequence has no effect on the amino acid sequence of the encoded protein and may also include nucleotide substitutions that result in one or more conservative amino acid substitutions in the encoded protein, which do not have a substantial effect on the function of the encoded protein. Whether or not a particular substitution may have a substantial effect can easily be determined by techniques known to one of ordinary skill in the art.

Inactivation of a gene may be achieved by mutagenesis methods such as by UV irradiation or by chemical mutagenesis such as treatment with N-methyl-N'-nitro-N-nitrosoguanidine or ethyl methane sulfonate, site-directed mutagenesis, homologous recombination, insertion-deletion mutagenesis (e.g., T-DNA insertion mutagenesis) or "Red-driven integration" (Datsenko, et al., (2000) Proc. Natl. Acad. Sci. USA, 97:6640-6645). One particular gene inactivation (knockout, KO) method used herein is T-DNA insertion mutagenesis. Other methods suitable to suppress and/or knockout expression of the TGD5 gene include the use of antisense, RNAi or siRNA suppression methods, as are known to one of ordinary skill in the art.

The terms "triacylglycerol" and "triglyceride" refer to a molecule comprising a glycerol backbone to which three acyl groups are esterified. This term may be represented by the abbreviation TAG. Standard representations of the fatty acids chain lengths and degrees of desaturation are used throughout as exemplified for example by: 18:0, 18:1, 18:2 and 18:3, which represent fatty acids having 18 carbon atom chains and which are fully saturated (18:0), or mono-, di-, and tri-unsaturated (18:1, 18:2 and 18:3, respectively).

General procedures for recombinant DNA technology and plant-related DNA technology are known in the art. See, for example, Sambrook, et al., Molecular Cloning: A Laboratory Manual, Third Edition, Cold Spring Harbor Press, 2001; US 2008/0282427 to Browse; Burgal, et al., (2008) Plant Biotechnology Journal 6:819-831; Lu, et al., (2006) The Plant Journal, 45:847-856.

In one embodiment of the present invention, it is contemplated that plants are engineered to produce and accumulate biological oils, particularly in vegetative, non-seed tissues. In a preferred embodiment, the oil comprises triacylglycerol (TAG). In the present invention, mutations to the TGD5 gene result in increased accumulation of biological oil in the vegetative tissues of the subject plant. In one embodiment, it is contemplated that the subject plant is any plant that naturally carries and expresses TGD5 genes or TGD5 gene homologs. Examples of such plants include, but are not limited to, various plant species including important crops such as tomato (*Solanum lycopersicum*), potato (*Solanum tuberosum*), barley (*Hordeum* sp.), poplar (*Populus* sp.), rice (*Oryza* sp.), cucumber (*Cucumis* sp.), sorghum (*Sorghum* sp.), soybean and other legumes, grasses (e.g., *Brachypodium distachyon*), grains (e.g., *Triticum urartu*), oilseed rape (*Brassica napus*) and other *Brassica* family members, and maize (*Zea* sp.). Most higher plant genomes surveyed have a TGD5 homolog while it appears that lower plant and non-plant genomes do not carry a gene homologous to TGD5. One of ordinary skill in the art can determine if a species of plant carries and expresses TGD5 genes or homologs thereof by using known molecular biological techniques. See, for example, Sambrook, et al., (2001). As is taught herein, mutations that reduce the amount of the protein produced or reduce or destroy the function of the encoded TGD5 protein result in increased fatty acid accumulation in the vegetative tissues of the subject plant.

In one embodiment, fatty acid synthesis in the vegetative tissues of a subject plant, as well as fatty acid retention, are enhanced in TGD5-deficient plants as compared to wild-type plants by over expression of additional genes encoding phospholipid:diacylglycerol acyltransferases (PDATs) or WRINKLED1 (WRI1). In another embodiment fatty acid retention in the subject plant is enhanced as compared to wild-type plants by over expression of genes encoding peptides or proteins related to protection of synthesized fatty acids from breakdown in the plant cells. Oleosins are a specific example of such proteins. In another embodiment, fatty acid accumulation is enhanced in TGD5-deficient plants by decreasing or knocking out the function of sugar-dependent 1 TAG lipase.

Gene Mutation

Chemical Mutagens

One of the TGD5 mutants of the present invention (tgd5-1) was generated by chemical mutagenesis of fad6 *Arabidopsis* seeds. There are many known chemical mutagens. Some resemble the bases found in normal DNA; others alter the structures of existing bases; others insert themselves (intercalate) in the helix between bases; while others work indirectly, creating reactive compounds that directly damage the DNA structure.

Ethyl methanesulfonate ($CH_3SO_3C_2H_5$; EMS), used herein (see below), is a mutagenic, teratogenic and, possibly, carcinogenic organic compound. It produces random mutations in genetic material by nucleotide substitution, particularly by guanine alkylation. This typically produces point mutations. EMS can induce mutations at a rate of $5\times10^{-4}$ to $5\times10^{-2}$ per gene without substantial killing. The ethyl group of EMS reacts with guanine in DNA, forming the abnormal base O-6-ethylguanine. During DNA replication, DNA polymerases that catalyze the process frequently place thymine, instead of cytosine, opposite O-6-ethylguanine. Following subsequent rounds of replication, the original G:C base pair can become an A:T pair (a transition mutation). This changes the genetic information, is often harmful to cells, and can result in altered phenotypes. EMS is often used in genetics as a mutagen. Mutations induced by EMS can then be characterized in genetic screens and other assays.

Radiation-Induced Mutagenesis

Gene mutations resulting from radiation-induced damage to DNA have been produced experimentally in many types of organisms. In general, the frequency of a given mutation increases in proportion to the dose of radiation in the low-to-intermediate dose range. At higher doses, however, the frequency of mutations induced by a given dose may be dependent on the rate at which the dose is accumulated, tending to be lower if the dose is accumulated over a long period of time.

Notwithstanding the fact that the vast majority of mutations are decidedly harmful, those induced by irradiation of seeds are frequently used by horticulturists and scientists as a means of producing new and improved varieties of plants. Mutations produced in this manner can affect such properties of the plant as early ripening and resistance to disease, with the result that economically important varieties of a number of species have been produced by irradiation. In their effects on plants, fast neutrons and heavy particles have been found to be up to about 100 times more mutagenic than X-rays. Radioactive elements taken up by plants also can be strongly mutagenic. In the choice of a suitable dose for the production of mutations, a compromise has to be made between the mutagenic effects and damaging effects of the radiation. As the number of mutations increases, so also does the extent of damage to the plants. In the irradiation of dry seeds by X-rays, a dose of 10 to 20 Gy may be given.

Genetically Engineered Mutations

Insertion mutagenesis is an alternative means of disrupting gene function (i.e., causing genetic mutations) and is based on the insertion of foreign DNA into the gene of interest. In *Arabidopsis*, this involves, for example, the use of either transposable elements (see, Parinov, et al. (1999) The Plant Cell, 11(12): 2263-2280) or T-DNA (transfer-DNA). T-DNA insertion is known to those of skill in the art as an effective method of mutating and inactivating target genes (Krysan, et al. (1999) The Plant Cell 11(12): 2283-2290; Radhamony, et al. (2005) Electronic Journal of Biotechnology 8(1):82-106; Wang (2008) J. Biochem. Tech. 1(1):11-20; US Patent Publication No. 2003/0079254 to Gelvin, all of which are incorporated herein by reference). T-DNA insertion mutagenesis is, in brief, the insertion of DNA elements that are able to insert at random within chromosomes. The T-DNA of *Agrobacterium tumefaciens* is one such example, although others are known to those of skill in the art. Feldmann and Marks (1987) Molecular and General Genetics, 208(3):1-9, which is incorporated herein by reference) devised a method for producing independent T-DNA transgenic lines via seed transformation.

Gene knockouts (KOs), or null mutations, are important because they provide a direct route to determining the function of a gene product in situ. Further, null mutations are effective in totally shutting off expression of a gene. The foreign DNA not only disrupts the expression of the gene into which it is inserted but also acts as a marker for subsequent identification of the mutation. Because *Arabidopsis* introns are small, and because there is very little intergenic material, the insertion of a piece of T-DNA on the order of 5 to 25 kb in length generally produces a dramatic disruption of gene function. If a large enough population of T-DNA transformed lines is available, one has a very good chance of finding a plant carrying a T-DNA insert within any gene of interest. Mutations that are homozygous lethal can be maintained in the population in the form of heterozygous plants. An advantage of using T-DNAs as the insertional mutagen, as opposed to transposons is that T-DNA insertions will not transpose subsequent to integration within the genome and are, therefore, chemically and physically stable through multiple generations.

Interfering RNA (e.g., RNAi, siRNA, microRNA, hpRNA, etc.) can be used to knockout or knockdown gene expression by altering posttranscriptional gene regulation in the target cell or organism through RNA degradation. Such methods are well known to one of ordinary skill in the art.

Methods to overexpress genes in organisms (e.g., plants) are known in the art as exemplified by, for example, Ausubel, et al., (1995) Short Protocols in Molecular Biology, 3rd ed., Wiley & Sons, and Sambrook, et al., (2001).

EXEMPLIFICATION

1. Generation of Mutants

The present application discloses a novel transporter TGD5 and use of inactive mutants thereof and phenotypic (e.g., down-regulated via interfering RNA) mutants thereof to boost storage TAG production and accumulation in vegetative tissues of plants. The TGD5 gene (At1g27695) and its putative role in lipid trafficking was identified by a forward genetic approach in the model plant *Arabidopsis*. The gene encodes a small glycine-rich protein of unknown function (FIG. 1). TGD5 gene homologs are present in various higher plant species.

Three TGD5 mutant *Arabidopsis* plants expressing mutated tgd5 genes are disclosed in the present application. One mutation was generated by chemical mutagenesis techniques. The other two mutants were generated using T-DNA insertion mutation technology.

TGD5 phenotypic mutants may be generated using RNAi constructs much as described for tgd1, tgd2, tgd3 and tgd4 in US Patent Application publication 2014/0228585 to Benning et al., the contents of which are incorporated by reference.

Chemical Mutagenesis

Approximately 40,000 *Arabidopsis* fad6 seeds were mutagenized with ethyl methane sulfonate using standard procedures as are known in the art (Xu et al. (2003) The EMBO Journal, 22(10):2370-2379). The resulting $M_1$ plants were allowed to self-pollinate. $M_2$ plants were grown under continuous light at 22° C. for three weeks and visually screened for a pale green appearance of their leaves. Small leaf samples were removed from three week old individual $M_2$ plants with pale green appearance and were used for determining the fatty acid composition by gas-liquid chromatography (GC). From approximately 25,000 plants screened in this way, six (6) pale green plants were identified that had marked increases in 18:1 at the expense of 18:3 leaf lipids. One of the pale green leaf mutant plants also accumulated trigalactosyldiacylglycerol (TGDG) in its leaves. Genetic complementation tests showed that the mutation in the genome was not allelic to previously identified tgd genes (i.e., those encoding TGD1, TGD2, TGD3 and TGD4). Thus, the strain was designated tgd5-1 fad6. The self-pollinated $F_1$ plants having the tgd5-1 mutation produced $F_2$ populations that segregated for pale-green leaf plants in a ratio of about 16 to 1 (26 out of 423, 6.15%) and all 26 pale green leaf plants accumulated TGDG in leaves and showed about two-fold increases in 18:1 and 18:2 with corresponding decreases in 18:3 in total leaf lipids.

The tgd5-1 mutation was outcrossed from the fad6 background to a wild type genomic background. A homozygous mutant in the wild type background in the $F_2$ generation, was used to investigate the biological consequences of the tgd5 mutation independent of fad6.

The mutation in tgd5-1 was identified by map-based cloning approach. The mutant contains a point mutation from G to A in the genomic sequence of At1g27695 at nucleotide 825 (FIG. 2). The mutated nucleotide is bold-faced and underlined. The mutant protein sequence is shown in FIG. 2 where the amino acid substitution is shown in bold face with underlining.

Biochemical Analysis of Mutants

An initial biochemical analysis of the all mutants was focused on fatty acid composition of leaf lipids as indicators of defects in lipid trafficking. For this purpose, polar lipids were separated by TLC and the fatty acid composition of individual lipid fractions was analyzed by GC as described (Xu C, et al., 2003). Detailed lipid analysis indicated that the some mutations specifically affected the known desaturases such as FAD3 and FAD7/8 as well as affecting genes encoding enzymes involved in galactolipid assembly. For further analysis, only mutants that appeared to be defective in the tgd5 gene encoding proteins involved in ER-to-plastid lipid transport were considered.

2. Characterization of the tgd5 Mutants

The tgd5-1 mutant identified in the screen from mutagenesis exhibited a decreased amount of 18:3 and increased amounts of 18:1 and 16:0 compared with the fad6 parent and the wild type (Columbia-2) strain. Analysis of the leaf fatty acid composition of MGDG and PE showed that they contained markedly reduced amounts of 18:3, whereas the relative amounts of 18:1 and 18:2 were increased in comparison with the fad6 parent plants and otherwise identical, wild type strains. The increase in 18:2 in PE indicated that the changes in fatty acid composition in the mutant were not due to deficiency in FAD2, the ER 18:1 desaturase. The possibility that the marked decrease in 18:3 could be due to deficiency in FAD7, which specifies the plastid 16:2/18:2 desaturase, was considered. A deficiency in FAD7 can be detected by substantial increases in 18:3 when mutant lines are grown at low temperature, because FAD8 specifies an enzyme, having the same specificity but which is expressed only during growth at low temperatures (Browse J, et al. (1986) Plant Physiology 81:859-864; McConn M, et al. (1994) Plant Physiol 106:1609-1614). The present mutant had only small increases in 18:3 (less than 5%) when grown at 18° C. compared with 28° C., suggesting that FAD7 was active.

Although the tgd5-1 fad6 line was capable of robust growth on soil and able to develop apparently normal flowers, it failed to produce seeds. Viable seeds were obtained when the mutant pollen was transferred onto wild type Columbia-2 (Col-2) pistils (but reciprocal transfer did not yield seeds). Self-pollinated $F_1$ plants produced $F_2$ populations that segregated for pale green plants with roughly twice the amount of 18:1 as found in the fad6 parent in a ratio of about 16 to 1, which was the expected frequency of the homozygous mutation (26 out of 423, 6.15%) in the fad6 background in these $F_2$ populations. On the basis of decreased levels of 18:3, the homozygous mutant line in the wild type background in the $F_2$ or $F_3$ generation was also identified, allowing the investigation of the biological consequences of the tgd5 mutations independently of fad6.

Prior to detailed phenotypic analysis, the mutant was backcrossed to the wild type strain, Columbia-2 (Col-2), three times. All subsequent experiments were carried out with the mutant gene in the Col-2 (wild type or parental) background. Following test crosses between the homozygous tgd5 mutant and wild type, all $F_1$ plants were indistinguishable. Of leaves removed from 106 $F_2$ plants from the cross between tgd5 and wild type, 23 (22%) contained substantially elevated levels of 18:1 and 18:2 with concomitant decreases in levels of 18:3, whereas fatty acid profiles of all other plants were indistinguishable from wild type. The approximately 3:1 segregation observed for $F_2$ plants was consistent with a single nuclear recessive mutation that results in elevated levels of 18:1 and 18:2 at the expense of 18:3 for the tgd5 mutant.

The growth phenotypes of several (see below) tgd5 mutants were examined and found to quite similar to the wild type. The leaves were slightly pale green in color compared to wild type and most of mutant plants appeared to bolt and flower earlier than the wild type. In addition to decreases in levels of 18:3 with concomitant increases in monounsaturated fatty acids and 18:2, the relative amounts of the major chloroplast lipids, MGDG and DGDG, were decreased, whereas the phospholipids PC and PE were more abundant in the mutant. Because the galactolipids are found primarily in the plastid and PE in the extraplastidic membranes, these lipid changes may likely reflect a decreased ratio of plastid-to-extraplastidic membranes in the mutants, consistent with the pale green appearance of mutant. The galactolipids in the mutant were characterized by an enrichment of C16 fatty acids, particularly for DGDG. The fatty acyl chains remaining esterified after position-specific lipase treatment of MGDG and DGDG (Xu C, et al., 2003) from the wild type and the tgd5 mutant was analyzed. It was apparent that 16-carbon fatty acids were highly enriched in the sn-2 position in the mutant, consistent with an enrichment of molecular species derived from the prokaryotic pathway. In other words, the eukaryotic pathway of galactolipid biosynthesis appeared to be disrupted in the tgd5 mutant, leading to a compensatory increase in the prokaryotic pathway.

3. Isolation of the Tgd5 Locus and Functional Analysis of the Encoded Protein

To determine the molecular basis for tgd5 mutant phenotypes, the tgd5-1 mutant (in the wild type, Columbia background) was crossed with wild type *Landsberg erecta*. The $F_1$ progeny were allowed to self-pollinate, and $F_2$ plants were used for mapping of the tgd5 mutation. Using a small mapping population of ~25 plants homozygous at the tgd5 locus (identified in the $F_2$ progeny on the basis of tgd5 lipid phenotype), the mutant locus was placed in the 5 cM interval on chromosome 1 between markers F13K9 and AZEPG. These two markers subsequently were used to score a mapping population of ~300 $F_2$ plants for recombinants in this interval and the tgd5 locus was mapped to an ≈200-kb region flanked by SSLP (Simple Sequence Length Polymorphisms) markers T7N9 and T22C5 (FIG. 3). This region of the *Arabidopsis* genome had not previously been recognized as encoding genes involved in lipid synthesis, modifications and trafficking. Sequencing of all the coding regions for the predicted 17 genes has been initiated. In the tgd5 segment, a G to A mutation in At1g27695 has been identified. This mutation resulted in the substitution of Gly by Asp in the TGD5 protein.

Independent evidence for the identity of tgd5 has been demonstrated through the analysis of two independent T-DNA KO lines for the gene in question. Homozygous plants for these lines have been isolated. Preliminary analysis indicated a similar leaf fatty acid profile between the T-DNA KO lines and the point mutant allele, i.e., increases in 16:0, 18:1 and 18:2 at the expense of 18:3 in comparison with the wild type. The point mutant allele was designated tgd5-1 and the two T-DNA alleles were designated tgd5-2 and tgd5-3. PCR experiments using cDNA from homozygous mutant plants showed that both T-DNA lines lack the full-length transcript that is present in tgd5-1 and wild type plants, but mRNA containing at least the first three of the four exons is present in tgd5-2. These results suggest that one may predict that tgd5-2 may be leaky, while tgd5-3 may likely be a null TGD5 mutant.

4. Characterization of Tgd5 Mutants

Detailed lipid profiling revealed that tgd5-1 was deficient in ER-derived thylakoid lipids and accumulates triacylglycerol (TAG) and trigalactosyldiacylglycerol in leaves, similar to the previously described tgd mutants (tgd 1, 2, 3, and 4). Additional analyses with two independent alleles containing T-DNA insertion mutations in the TGD5 gene confirmed the findings with the chemically induced (tgd5-1) mutant.

T-DNA Generated Knockout Mutants

Two T-DNA insertion mutations in the TGD5 gene were generated. Procedures for T-DNA insertion mutagenesis in plants are well known to those of ordinary skill in the art. See, for example, Radhamony, et al., 2005; Krysan, et al., 1999 and Parinov, et al., 1999). The gene specific primers used were: 5'-gctagttgctatgggatg-3' [SEQ ID NO: 5] and 5'-cgggtttcattgagcaatc-3' [SEQ ID NO: 6]. The T-DNA left border primer used was: 5'-gcgtggaccgcttgctgcaac-3' [SEQ ID NO: 7].

The mutants that were generated were designated tgd5-2 and tgd5-3. DNA sequencing revealed that the tgd5-2 and tgd5-3 mutants harbor T-DNA insertions at nucleotides 930 and 639 of the genomic sequence [SEQ ID NO: 1], respectively (see FIG. 1).

5. TAG Production

Figure 4:
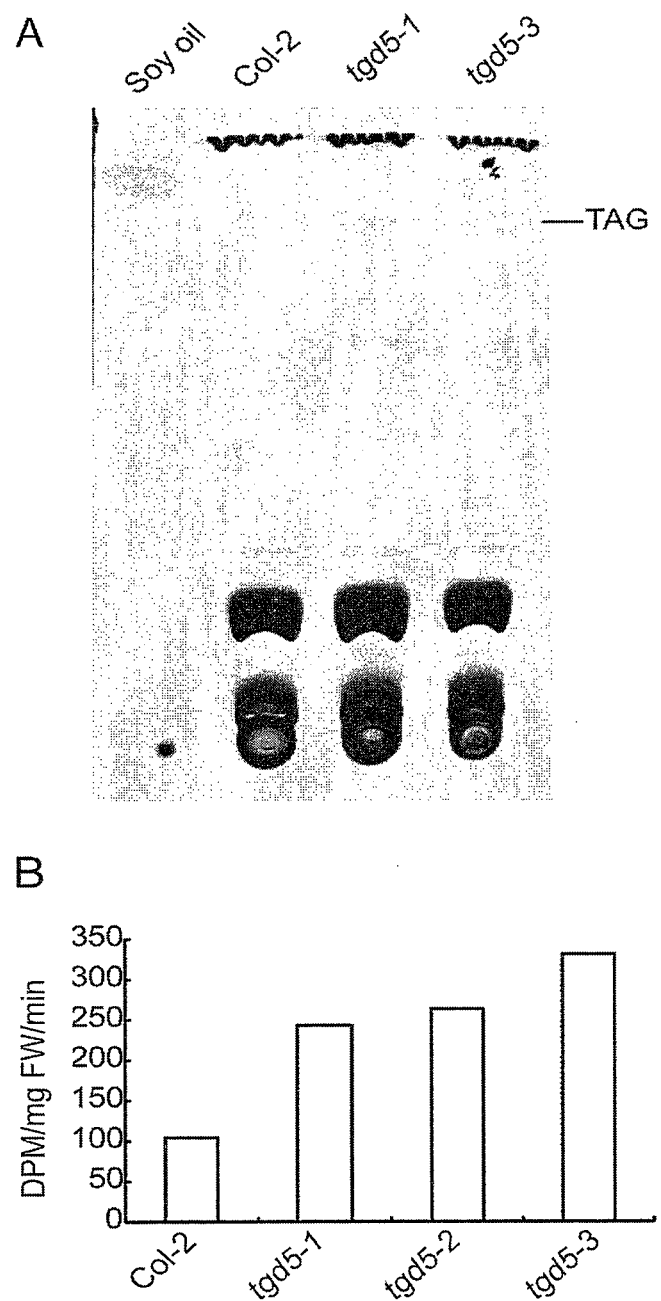
FIG. 4 shows (A) thin layer chromatography (TLC) results for the leaves of plants bearing the tgd5-1 and tgd5-3 mutant genes and (B) fatty acid synthesis enhancement in leaves of plants having the tgd5-1, tgd5-2, and tgd5-3 mutant genes.

The tgd5 mutants accumulate TAG in leaves and have enhanced fatty acid synthesis in leaves (FIG. 4). Specifically, the tgd5 mutants accumulate TAG in vegetative tissues of *Arabidopsis* (FIG. 4) at levels about 10 times higher than wild type. One important difference between tgd5 mutants and other TGD (tgd 1, 2, 3, and 4) mutants is that tgd5 mutants (e.g., knockout mutants) germinate, grow and reproduce almost as well as the wild type. Remarkably, inactivation of TGD5 leads to a 3-fold higher rate of fatty acid synthesis (FIG. 4). However, in spite of the increase in fatty acid synthesis and increase in TAG, the total lipid content remained unaltered in tgd5 mutants compared with wild type, suggesting activation of a futile cycle of fatty acid synthesis and breakdown due to disruption of TGD5.

Figure 5:
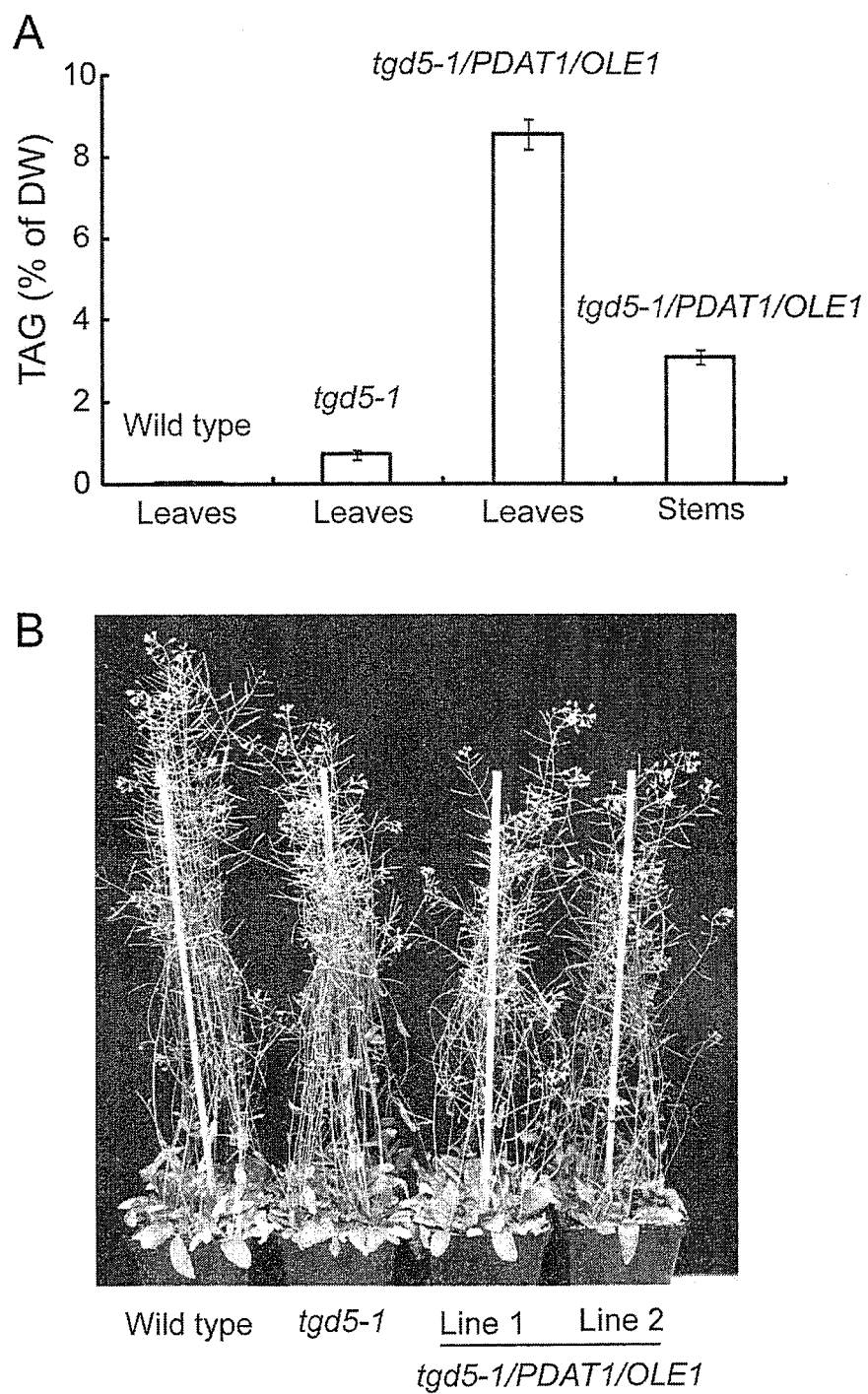
FIG. 5 shows TAG content (A) and growth phenotype (B) of transgenic lines overexpressing PDAT1 and OLE1 in the tgd5-1 mutant background.

Since the rate of fatty acid synthesis is dramatically enhanced in tgd5 mutants, one attractive approach to increase TAG accumulation in vegetative tissues was to co-express phospholipid:diacylglycerol acyltransferase (PDAT) to channel fatty acids into TAG and oleosin to build up a storage compartment for TAG and therefore to prevent the futile cycle of fatty acid synthesis and breakdown. To this end, PDAT1 and OLE1 (both from *Arabidopsis*) were overexpressed in the tgd5-1 mutant in double transgenic plants carrying PDAT1 and OLE1 expression constructs. Analysis of TAG content revealed an over 246-fold increase to 8.5% of dry weight in leaves of double transgenic plants in the tgd5-1 mutant background (FIG. 5). In addition, TAG also accumulates in stems to 3.1% of dry weight. Importantly, despite a major investment of resources towards TAG synthesis and storage, the growth and development of the double transgenic plants are not significantly altered (FIG. 5) and over 95% of the transgenic seeds germinate on soil.

Decreasing breakdown of TAG represents an attractive alternative way in which to increase TAG accumulation in the tgd5 mutants. Thus, a cross between the tgd5-3 T-DNA null mutant and a T-DNA insertion mutant disrupted in SUGAR-DEPENDENT1 (SDP1) TAG lipase (sdp1-4) was made because SDP1 has been shown to be responsible for initiating TAG breakdown during early seedling establishment (Eastmond, 2006). Microscopic examination of mature leaves stained with the neutral lipid-specific dye, Nile red, revealed a dramatic increase in the size of lipid droplets in the tgd5-3 sdp1-4 double mutant, compared with either parent. Quantification of leaf lipid extracts from 7-week-old soil-grown plants showed that the amounts of leaf TAG increased to 8.0% per dry weight in the double mutant, a 114- and 6.7-fold increase compared with the wild type and tgd5-3, respectively.

6. Materials and Methods

Plant Materials and Growth Conditions

The *Arabidopsis* (*Arabidopsis thaliana*) plants used in this study were of the Columbia ecotype. For growth on agar plates, surface-sterilized seeds of *Arabidopsis* were germinated on 0.6% (w/v) agar-solidified half-strength MS (Murashige et al. (1962) Physiol. Plant. 15:473-497) medium supplemented with 1% (w/v) sucrose in an incubator with a photon flux density of 80-100 µmol m$^{-2}$ s$^{-1}$ and a light period of 16 h (22° C.) and a dark period of 8 h (18° C.). For growth on soil, plants were first grown on MS medium for 10 days and then transferred to soil and grown under a photosynthetic photon flux density of 150-200 µmol m$^{-2}$ sec$^{-1}$ at 22/18° C. (day/night) with a 16 h light/8 h dark period.

Generation of Plant Expression Vectors and Plant Transformation

The full-length coding regions of PDAT1 (At5g13640) were amplified by RT-PCR using the primers 5'-GCGTGG-TACCATGCCCCTTATTCATCGGA-3' [SEQ ID NO: 8] and 5'-ACGTCTGCAGTCACAGCTTCAGGT-CAATACGCTC-3' [SEQ ID NO: 9]. The resulting PDAT1 PCR product was digested with KpnI/PstI and inserted into the respective sites of a binary vector derived from pPZP212 (Hajdukiewicz et al. (1994) Plant Mol. Biol. 25:989-994). To generate the OLE1 and OLE1-GFP fusion constructs, the entire genomic DNA encoding the *Arabidopsis* OLE1 (At4g25140) was amplified and ligated into pCR8 TOPO-cloning entry vector (Invitrogen). The gene was then fused with GFP in-frame at the C-terminus through LR reaction to the destination vector pGKPGWG (Zhong et al. (2008) Transgenic Research 17:985-989). After confirming the integrity of the constructs by sequencing, plant stable transformation was performed according to Clough and Bent (Plant J. 16:735-743 (1998)). Transgenic plants were selected in the presence of the respective antibiotics for the vectors on MS medium lacking sucrose.

Lipid and Fatty Acid Analyses

Plant tissues were frozen in liquid nitrogen and total lipids were extracted by homogenization in chloroform/methanol/formic acid (1:1:0.1, by volume) and 1 M KCl-0.2 M $H_3PO_4$ as taught by Dormann et al. (Plant Cell 7:1801-1810 (1995)). Neutral and total polar lipids were separated on silica plates (Si250 with pre-adsorbent layer; Mallinckrodt Baker) by thin layer chromatography using a solvent system of hexane-diethyl ether-acetic acid (70:30:1, by volume). Lipids were visualized by spraying 5% $H_2SO_4$ followed by charring. For quantitative analysis, lipids were visualized by brief exposure to iodine vapor and identified by co-chromatography with lipid standards. Individual lipids were scraped from the plate and used to prepare fatty acid methyl esters. Separation and identification of the fatty acid methyl esters (FAMEs) was performed on an HP5975 gas chromatography-mass spectrometer (Hewlett-Packard, Palo Alto, Calif.) fitted with 60 m×250 µm SP-2340 capillary column (Supelco, Bellefonte, Pa.) with helium as a carrier gas. The methyl esters were quantified using heptadecanoic acid as the internal standard as described by Fan et al. (FEBS Lett. 585:1985-1991 (2011)). The TAG content was calculated as taught by Li, et al. (Phytochemistry 67:904-915 (2006)).

The invention claimed is:

1. A composition comprising the nucleotide sequence SEQ ID NO: 3.

2. A composition comprising the amino acid sequence SEQ ID NO: 4.

3. A composition comprising the nucleotide sequence SEQ ID NO: 3 or the amino acid sequence SEQ ID NO: 4 that results in diminished trigalactosyldiacylglycerol-5 (TGD5) protein function or activity as compared to an otherwise identical plant.

4. The composition of claim 3 wherein said composition is a plant, progeny having the same genotype as the plant, or seeds having the same genotype as the plant.

5. The plant of claim 4 further comprising an increased copy number selected from the group consisting of genes encoding phospholipid: diacylglycerol acyltransferase (PDAT), genes encoding oleosin (OLE), genes encoding WRINKLED1 (WRI1), and combinations thereof.

6. The plant of claim 5 further comprising an increased copy number of genes encoding phospholipid:diacylglycerol acyltransferase (PDAT), and an increased copy number of genes encoding oleosin (OLE), and an increased copy number of genes encoding WRINKLED1 (WRI1).

7. The plant of claim 4 further comprising a defective sugar-dependent 1 TAG lipase gene (sdp1).

8. The plant of claim 4 wherein diminished amounts of wild type TGD5 as compared to wild type amounts of wild type TGD5 are expressed.

9. A method for increasing production and retention of oil in vegetative tissues of a plant, the method comprising: providing a plant comprising: a) the nucleotide sequence SEQ ID NO: 3 or the amino acid sequence SEQ ID NO: 4, and further comprising b) increased expression levels of a gene encoding phospholipid:diacylglycerol acyltransferase (PDAT), and c) increased expression levels of a gene encoding oleosin (OLE); and growing said plant to accumulate oil in vegetative tissues of said plant.

10. The method of claim 9, additionally comprising extracting said oil from said plant.

11. A method for enhancing the caloric content of vegetative tissue of a plant comprising: providing a plant comprising the nucleotide sequence SEQ ID NO: 3 or the amino acid sequence SEQ ID NO: 4; and growing said plant to accumulate in vegetative tissues of said plant.

12. A method for enhancing the caloric content of vegetative tissue of a plant comprising: providing a plant comprising the nucleotide sequence SEQ ID NO: 3 or the amino acid sequence SEQ ID NO: 4 and further comprising a defective sugar-dependent1 TAG lipase (sdp1) gene; and growing said plant to accumulate oil in vegetative tissues of said plant.

* * * * *